United States Patent [19]
Kelley et al.

[11] Patent Number: 6,039,710
[45] Date of Patent: Mar. 21, 2000

[54] APPARATUS FOR PROVIDING FACIAL SUPPORT

[75] Inventors: David E. Kelley, Santa Monica; Jeffrey C. Kramer, Sherman Oaks; Jonathan L. Pontell, Beverly Hills; Loretta S. Parral, Studio City; Michelle V. Roth, Venice; Anoush Yergen, Studio City; Arlene Sanford, Los Angeles, all of Calif.

[73] Assignee: Twentieth Century Fox Film Corporation, Los Angeles, Calif.

[21] Appl. No.: 08/939,694

[22] Filed: Sep. 29, 1997

[51] Int. Cl.[7] ................................ A61F 13/12
[52] U.S. Cl. .............................. 602/74; 128/857
[58] Field of Search .................. 602/5, 17, 60, 602/61, 74; 128/857; 2/423, 424, 9, 206; 604/303

[56] References Cited

U.S. PATENT DOCUMENTS

| | | | |
|---|---|---|---|
| 1,291,846 | 1/1919 | Greenfield | 2/206 |
| 1,693,452 | 11/1928 | McCune | 604/303 |
| 1,996,703 | 4/1935 | Giuliano | 604/303 |
| 2,024,491 | 12/1935 | Veysey | 602/79 |
| 3,709,225 | 1/1973 | Sobel | 128/DIG. 15 |
| 3,804,087 | 4/1974 | Sarnoff | 128/163 |
| 3,832,995 | 9/1974 | Welch | 128/24.1 |
| 4,207,881 | 6/1980 | Richter | 128/89 |
| 4,577,627 | 3/1986 | Facal Garcia | 128/76 |
| 4,635,625 | 1/1987 | Teeple | 128/163 |
| 4,650,182 | 3/1987 | Ross | 272/95 |
| 4,658,811 | 4/1987 | Beaird | 606/204.35 |
| 4,823,778 | 4/1989 | Ewing | 128/76 |
| 4,832,333 | 5/1989 | Lockett | 272/94 |
| 4,856,535 | 8/1989 | Forbes | 128/857 |
| 4,892,092 | 1/1990 | Klein | 128/76 |
| 4,934,357 | 6/1990 | Frantzich et al. | 128/164 |
| 4,965,887 | 10/1990 | Pauluccio et al. | 2/9 |
| 5,031,609 | 7/1991 | Fye | 128/163 |
| 5,035,420 | 7/1991 | Beeuwkes, III et al. | 272/95 |
| 5,074,297 | 12/1991 | Venegas | 128/204.18 |
| 5,080,092 | 1/1992 | Tenna | 128/201.19 |
| 5,116,675 | 5/1992 | Nash-Morgan | 428/343 |
| 5,242,347 | 9/1993 | Keeton | 482/102 |
| 5,350,418 | 9/1994 | Janevski et al. | 607/111 |
| 5,396,881 | 3/1995 | Klein | 601/23 |
| 5,477,998 | 12/1995 | Reckler | 224/151 |
| 5,484,359 | 1/1996 | Wabafiyebazu | 482/11 |
| 5,499,966 | 3/1996 | Bulley et al. | 602/42 |
| 5,501,646 | 3/1996 | Miller | 482/11 |
| 5,527,357 | 6/1996 | Springer, Jr. | 607/140 |

FOREIGN PATENT DOCUMENTS

| | | |
|---|---|---|
| 2046099 | 7/1991 | Canada . |
| WO 94/20051 | 9/1994 | WIPO . |

OTHER PUBLICATIONS

"Wrinkle Ease," *Beauty FX*, http://www.beautyfx.com, Sep. 10, 1997.

Storey, Kristin, "Beauty Tips; Chin Up: You Can Get Face–Lift with Elastic Band Therapy, Not Surgery," *The Detroit News*, www.detnews.com/menu/stories/42360.htm, Apr. 3, 1996.

*Primary Examiner*—Richard J. Apley
*Assistant Examiner*—Denise Pothier
*Attorney, Agent, or Firm*—Fliesler, Dubb, Meyer & Lovejoy LLP

[57] ABSTRACT

An apparatus for providing facial support includes a head band, a head strap, a cheek support, a forehead strap and a nose band. The head band wraps around the top of the head and the chin. The cheek support is attached to the head band and provides support for the cheeks. The nose strap and the forehead band hold the apparatus in place on the user's face. The head strap is used to hold the apparatus on the face and to pull the cheek support into engagement with the cheeks. By applying support to the cheeks, sagging of the cheeks can be reduced or prevented.

17 Claims, 3 Drawing Sheets

APPARATUS FOR PROVIDING FACIAL SUPPORT

BACKGROUND OF THE INVENTION

1. Field of the Invention

The present invention is directed to an apparatus for providing facial support.

2. Description of the Related Art

As people grow older, their skin loses elasticity and their facial muscles loose tone causing the face to wrinkle and/or sag. Some of the areas of the face most affected include the chin and the cheeks. This aging effect can be further accelerated by activities that include vertical motion and impact, such as jogging, aerobic exercises and various other activities that require repetitive jumping.

For example, jogging is one of the leading causes of wrinkles and sagging skin. When a person jogs, the skin on the face moves up and down causing the skin to stretch, lose its elasticity and eventually sag and/or wrinkle. Additionally, facial muscles can deteriorate. All of these effects can cause premature aging of the face.

Currently, there are no solutions to prevent the above described premature aging of the face. Support bandages exist to provide support to parts of the face and head after oral and cosmetic surgeries. However, these support bandages would not be effective to prevent the premature aging described above. These support bandages do not cover the cheeks, do not provide any support for the cheeks and do not hold the cheeks in place during strenuous activities such as jogging.

Various exercise machines are available to maintain the tone of the facial muscles. These exercise machines have not been successful because they are uncomfortable to use and many people simply do not like to use exercise machines. Additionally, these machines do not provide support for the face.

Therefore, an apparatus is needed that can aid in the prevention of premature aging from sagging skin and/or wrinkles.

SUMMARY OF THE INVENTION

The present invention, roughly described, includes an apparatus for providing facial support. The apparatus includes a head band, cheek support, head strap, nose strap and forehead strap. The head band is designed to wrap around a human head so that a portion of the head band is below the jaw. The cheek support is attached to the head band at two or more locations such that the cheek support alone or in combination with the head band cover and support substantially all of both cheeks on the face. The cheek support and the head band define an aperture for the mouth between the cheek support and head band. The head strap attaches to two locations on the head band. The head band is designed to fit behind the human head. When the head strap is secured behind the head, it pulls on the head band and the cheek support, causing the cheek support to apply a force to the cheeks. The nose strap is attached to the cheek support at two locations. The nose strap engages the nose and, with the cheek support, defines an aperture for the nose. That is, the nose aperture is below the nose strap and above the cheek support. The forehead strap is connected to the head band at two locations. The forehead strap is designed to lie across the forehead and aid in holding the apparatus in place. Below the forehead strap and above the nose strap is an aperture for the eyes.

In one embodiment, the head band, cheek support, head strap and forehead strap are made of a soft stretchable mesh material. In one alternative these components are partially transparent. The cheeks support can include means to allow moisture to evaporate from the skin. One example of such a means is to manufacture the cheek support from a mesh material such that there are tiny apertures in the cheek support. The various components mentioned above can be separate units that are attached using any of various means. For example, the components can be attached at an elastic band using conventional stitching, can be attached without an elastic band using conventional stitching or any other means known in the art. In another embodiment, two or more of the components can be a single structure. Both the head strap and head band include two portions which attach together using VELCRO™. The portions can be unattached to allow the apparatus to be easily removed from and placed on the head. Additionally, the velcro is used to adjust the size of the apparatus. A further alternative includes attaching one or more pads to the cheek support such that the pad engages one or more of the cheeks and apply moisturizer or other facial creams to the cheeks.

These and other objects and advantages of the invention will appear more clearly from the following detailed description in which the preferred embodiment of the invention has been set forth in conjunction with the drawings.

DETAILED DESCRIPTION

Figure 1:
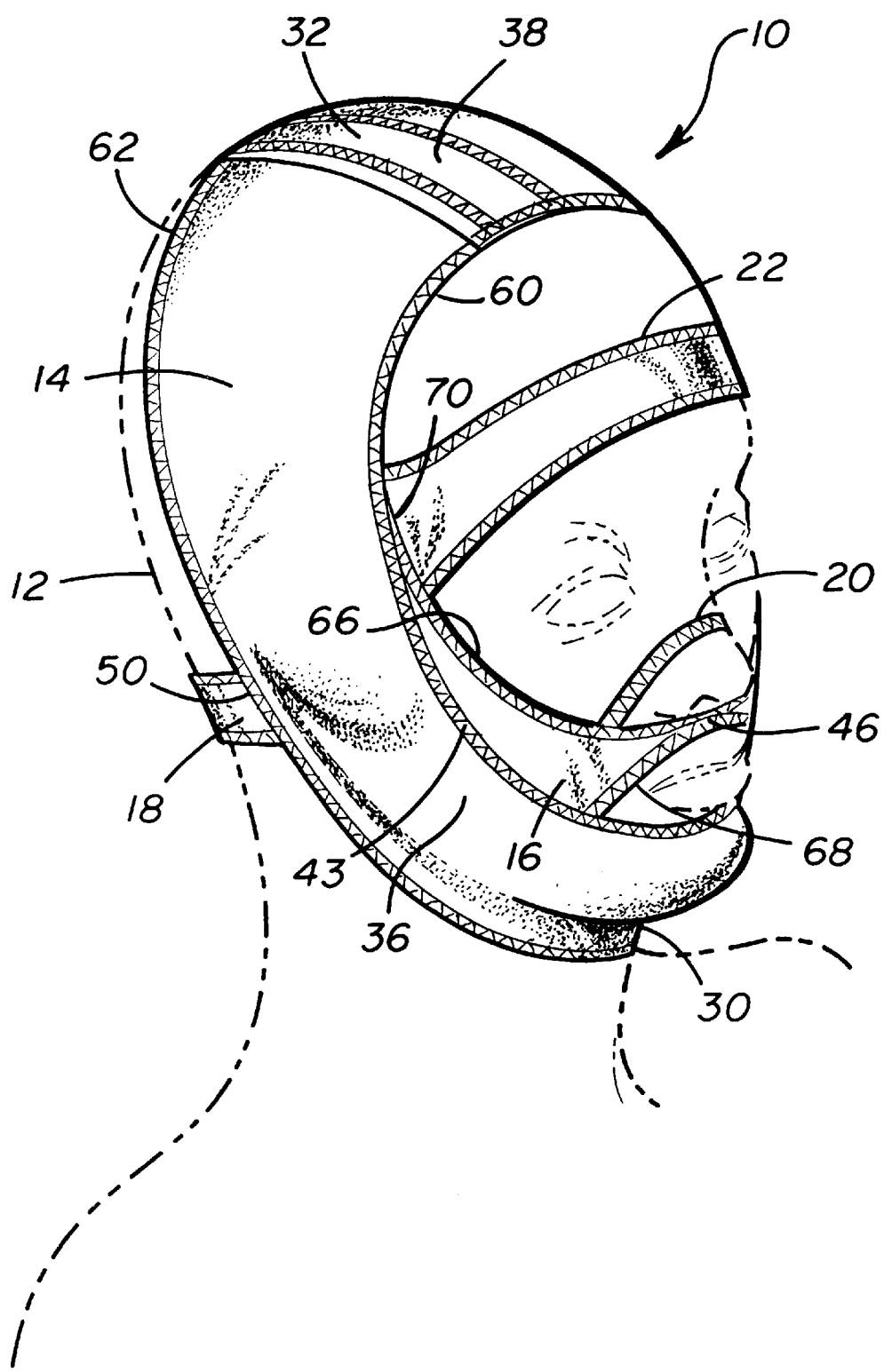
FIG. 1 is a front perspective view of the present invention fitted on a human head.
Figure 3:
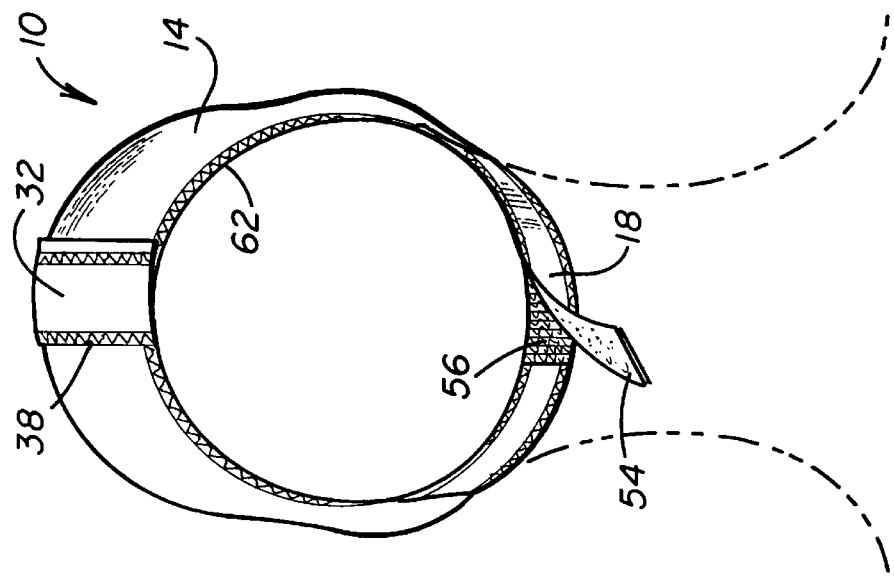
FIG. 3 is a rear view of the present invention fitted on a human head.
Figure 2:
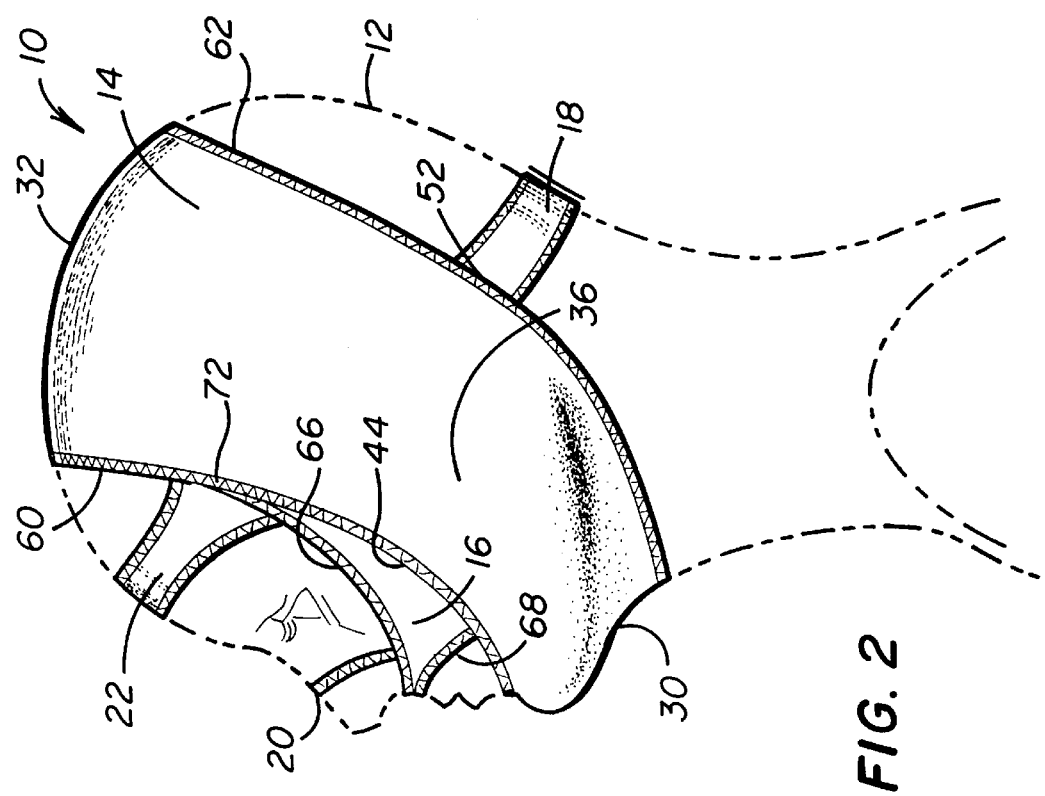
FIG. 2 is side view of the present invention fitted on a human head.
Figure 4:
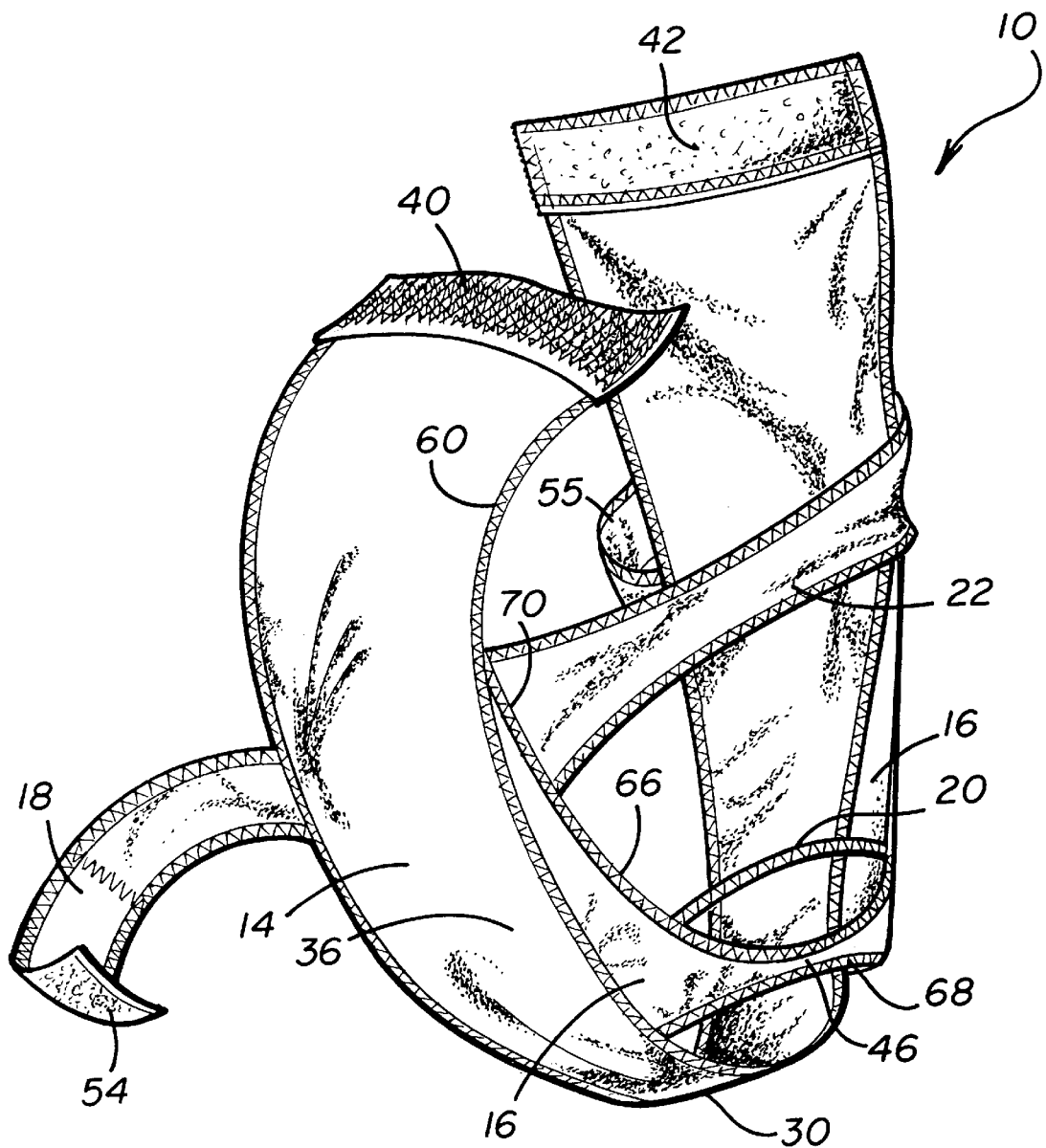
FIG. 4 is a front perspective view of the present invention, without showing a human head.

FIGS. 1–4 show apparatus 10 for providing facial support. FIGS. 1–3 shows apparatus 10 fitted on a human head 12. The apparatus includes head band 14, cheek support 16, head strap 18, nose strap 20 and forehead strap 22. Head band 14 wraps around head 12. The bottom 30 of head band 14 lies below the chin and applies a force pushing up against the chin and the bottom of the jaw. The top 32 of head band 14 engages the top of head 12. The width of the top 32 of head band 14 is approximately 12 centimeters. At the bottom 30, head band 14 is approximately 6.5 cm. wide. Between top 32 and bottom 30, head band 14 tapers from 12 cm. to 6.5 cm. in width. At locations 36, head band 14 engages the cheeks and provides some support for the cheeks. Note that head band 14 covers and supports the ears as shown in FIGS. 1 and 2. At top 32 of head band 14 is a velcro section 38. Velcro section 38 includes a first side 40 and a second side 42 (See FIG. 4). Velcro section 38 is opened to allow the apparatus to be easily removed from and placed on head 12. In one embodiment, velcro 38 can be used to adjust the size of head band 14 by uniting sides 40 and 42 in different orientations.

Cheek support 16 is used to engage and support the cheeks of head 12. Cheek support 16, in combination with section 36 of head band 14, covers and supports substantially all of both cheeks of head 12. The term "substantially all" indicates that it is not necessary that the entire cheek be covered. However, almost all of the cheek should be covered so that enough of the cheek is covered and supported to prevent the negative effects from the vertical impact as discussed above, for example, from such activities as jogging. The phrase "cheek support 16, in combination with section 36 of head band 14," indicates (1) cheek support 16 by itself or (2) a combination of cheek support 16 and section 36 of head band 14.

Cheek support 16 has two ends 43 (FIG. 1) and 44 (FIG. 2). End 43 is connected to head band 14 at one section of the head band 14 and end 44 is connected to a second and different section of head band 14. Cheek support 16 tapers from a width of 12 cm. at ends 43 and 44 down to 1 cm. at middle 46 of cheek support 16. In between cheek support 16 and head band 14 is an aperture for the mouth. In one embodiment, cheek support 16 covers the cheekbones.

Bordering the length of head band 14 are two elastic bands 60 and 62. Both elastic bands are stitched to head band 14 using conventional stitching known in the art. Bordering the length of cheek support 16 are two elastic bands 66 and 68, which are stitched to cheek support 16. Cheek support 16 is attached to head band 14 by having ends 43 and 44 stitched to separate locations on elastic band 60 (FIGS. 1 and 2).

Head strap 18 is connected to head band 14 by stitching ends 50 and 52 to separate locations on elastic band 62. (See FIGS. 1 and 2). Head strap 18 is made up of two straps. The first strap has a velcro portion 54 at its end. The second strap has a velcro portion 56 at its end. The two velcro portions are designed to attach to each other. Opening up velcro ends 54 and 56 allows the apparatus to be easily removed from and placed on human head 12. In one embodiment, velcro ends 54 and 56 can be used to adjust the sizing of strap 18. Head strap 18 is 20 cm. long and 3½ cm. wide. When apparatus 10 is placed on head 12 and head strap 18 is sufficiently secured, head strap 18 pulls back on head band 14 which causes portion 36 and cheek support 16 to press up against and apply pressure to the cheeks. Head strap 18 is bordered by two elastic bands running along the length of head strap 18.

Nose band 20 includes an elastic band with stitching running through the band. Nose strap 20 is approximately 6 cm. long. Nose band 20 attaches to cheek support 16 at a first location on band 66 and the second location on band 66 such that nose strap 20 fits over the bridge of the nose. The nose sits below nose strap 20 and above cheek support 16. In one alternative, the nose strap is connected to head band 14.

Forehead strap 22 is approximately 14.5 cm. long. Forehead strap 22 is 4 cm. wide at its ends and tapers down to 2.8 cm. at the middle of the strap. Forehead strap 22 connects to band 66 at two separate locations 70 and 72. In another alternative forehead strap 22 can be connected to band 60 or other parts of cheek support 16 or head band 14. Forehead strap 22 is bordered by two elastic bands running along the length of forehead strap 22. Between nose strap 20 and forehead strap 22 is an aperture for the eyes. Both nose strap 20 and forehead strap 22 are used to hold apparatus 10 in proper placement on head 12.

The inventors contemplate that some embodiments would not include nose strap 20 and forehead strap 22. Rather, the user would be required to properly place the apparatus onto the head.

All the numbers given for dimensions can be changed to alter the size of apparatus 10. Another way of adjusting the size of the apparatus 10 is by using materials that can be stretched. In one embodiment, head band 14, face support 16, head strap 18 and forehead strap 22 are made of a soft, stretchable mesh (e.g., power mesh). This material can stretch such that the shape of the components will adjust to the contour of the head and/or face. Additionally, a mesh material, because of all the tiny apertures, will allow the skin below the material to cool faster and will allow moisture (e.g., such as perspiration) to evaporate quicker. Other suitable soft, stretchable materials can also be used. In other embodiments, some of the components can be made of the soft stretchable mesh material and others can be made of a material that is not mesh, that is not stretchable or that is not soft.

In one alternative, one or more pads can be attached to either cheek support 16 or head band 14 such that the pads are engaging the cheeks of the user. The pad can then be treated to apply moisturizer, skin cream, minerals, medicine or other chemicals to the cheeks. The pad can also be placed on other areas of apparatus to engage other portions of the face or head.

In one alternative, two or more of the various components (14, 16, 18, 20 and 22) can be manufactured as a single structure rather than being separate components that are attached together. For example, head band 14 and cheek support 16 can be one structure. Similarly any other combination of two or more of the elements (14, 16, 18, 20 and 22) can be combined and manufactured as a single structure, or all of the elements can be combined as one single structure.

In one embodiment, the mesh (or other material) used to make the components is partially transparent. That is, the size of the apertures and the number of the apertures allow a person to see through the components and see the skin below. Other materials that are partially transparent may also be used. In some alternatives, the apparatus can be designed to be more visible. For example, apparatus 10 can be white or a flourescent color. For night use, the materials used to make one or more of the components can be lined with reflective materials.

The foregoing detailed description of the invention has been presented for purposes of illustration and description. It is not intended to be exhaustive or to limit the invention to the precise form disclosed, and obviously many modifications and variations are possible in light of the above teaching. The described embodiment was chosen in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. An apparatus for providing facial support, comprising:
a first band having a first portion, said first band configured to wrap around a human head and said first portion configured to be below a jaw of the human head, said first band being made of a soft stretchable material;
a cheek support separate from and attached to said first band, said cheek support being made of a soft stretchable material, said cheek support and said first band define an aperture for a mouth, said cheek support includes a middle portion and two cheek portions, said middle portion is located between said cheek portions, said cheek portions are configured to cover and support at least a portion of both cheeks on the human head, said cheek portions are tapered toward said middle portion; and
a first strap attached to said first band, said first strap designed to fit behind the human head and cause said cheek support to apply a force to both cheeks on the human head.

2. An apparatus according to claim 1, further including:

a nose strap connected to one of either said first band or said cheek support, said nose strap and said cheek support define an aperture for a nose.

3. An apparatus according to claim 1, further including:

a forehead strap connected to said first band at two or more locations, said forehead strap designed to engage a forehead of the human head and aid in holding said apparatus in place.

4. An apparatus according to claim 1, further including:

a nose strap connected to one of either said first band or said cheek support, said nose strap and said cheek support define an aperture for a nose; and a forehead strap connected to said first band, said forehead strap designed to engage a forehead of the human head and aid in holding said apparatus in place, said nose strap and said forehead strap define an aperture for eyes.

5. An apparatus according to claim 1, wherein:

said cheek support includes means to allow moisture to evaporate from skin.

6. An apparatus according to claim 1, wherein:

said first band is partially transparent.

7. An apparatus according to claim 1, wherein:

said first strap includes a first attaching portion and a second attaching portion, said first attaching portion being removably attached to said second attaching portion.

8. An apparatus according to claim 1, wherein:

said first band includes a first attaching portion and a second attaching portion, said first attaching portion being removably attached to said second attaching portion.

9. An apparatus according to claim 1, further including:

a pad attached to said cheek support to engage one of the cheeks and apply moisturizer to said one of the cheeks.

10. An apparatus according to claim 1, further including:

a pad attached to said cheek support to engage one of the cheeks and apply skin cream to said one of the cheeks.

11. An apparatus according to claim 1, wherein:

said first band includes reflective materials.

12. An apparatus for providing facial support, comprising:

a first band having a first portion, said first band configured to wrap around a human head and said first portion configured to be below a jaw of the human head, said first band being made of a soft stretchable material;

a cheek support separate from and coupled to said first band, said cheek support and said first band define an aperture for a mouth, said cheek support is configured to cover and support at least a portion of one or more cheeks on the human head, said cheek support comprising a soft stretchable material and a first elastic band, said soft stretchable material having a length, said first elastic band is separate from and attached to said soft stretchable material along said length; and a first strap attached to said first band, said first strap designed to fit behind the human head and cause said cheek support to apply a force to one or more cheeks on the human head.

13. An apparatus according to claim 12, wherein:

said cheek support includes a second elastic band, a first edge and a second edge, said first elastic band is attached along said first edge and said second elastic band is attached along said second edge.

14. An apparatus according to claim 12, wherein:

said first band includes a second elastic band, said cheek support is attached to said second elastic band.

15. An apparatus according to claim 12, wherein;

said cheek support includes a middle portion and two end portions, said middle portion having a width smaller than said two end portions such that said cheek support is tapered toward said middle portion.

16. An apparatus for providing facial support, comprising:

a first band having a first portion, said first band configured to wrap around a human head and said first portion configured to be below a jaw of the human head, said first band being made of a soft stretchable material;

an elastic band separate from and attached to said first band;

a cheek support separate from and attached to said first band, said cheek support in combination with said first band is configured to cover and support at least a portion of both cheeks on the human head, said cheek support and said first band define an aperture for a mouth, said first band and said cheek support are attached at said elastic band; and a first strap attached to said first band, said first strap designed to fit behind the human bead and cause said cheek support to apply a force to both cheeks on the human head.

17. An apparatus for providing facial support, comprising:

a first band having a first portion, said first band configured to wrap around a human head and said first portion configured to be below a jaw of the human head, said first band being made of a soft stretchable material;

a cheek support separate from and attached to said first band such that said cheek support in combination with said first band is configured to cover and support substantially all of both cheeks on the human head, said cheek support and said first band define an aperture for a mouth, said cheek support includes a middle portion and two end portions, said middle portion having a width smaller than said two end portions;

an elastic band, said first band and said cheek support are attached at said elastic band; and a first strap attached to said first band, said first strap designed to fit behind the human head and cause said cheek support to apply a force to both cheeks on the human head.

* * * * *

UNITED STATES PATENT AND TRADEMARK OFFICE
CERTIFICATE OF CORRECTION

PATENT NO. : 6,039,710
DATED : March 21, 2000
INVENTOR(S) : Kelley, et al.

It is certified that error appears in the above-identified patent and that said Letters Patent is hereby corrected as shown below:

Col. 6, line 34: after "human" and before "and" delete "bead" and substitute therefor --head--

Signed and Sealed this

Twenty-second Day of May, 2001

Attest:

NICHOLAS P. GODICI

Attesting Officer

Acting Director of the United States Patent and Trademark Office